United States Patent [19]

Day et al.

[11] Patent Number: 5,403,573
[45] Date of Patent: Apr. 4, 1995

[54] RADIOLABELED PROTEIN COMPOSITION AND METHOD FOR RADIATION SYNOVECTOMY

[75] Inventors: Delbert E. Day, Rolla; Gary J. Ehrhardt; Kurt R. Zinn, both of Columbia, all of Mo.

[73] Assignee: The Curators of the University of Missouri, Columbia, Mo.

[21] Appl. No.: 872,899

[22] Filed: Apr. 23, 1992

[51] Int. Cl.$^6$ ............................................. A61K 43/00
[52] U.S. Cl. .................................. 424/1.29; 424/1.37; 424/1.49; 424/169
[58] Field of Search ........ 424/1.1, 489, 499, 1.29.1.37, 424/1.69, 1.49; 534/10; 423/49, 50

[56] References Cited

U.S. PATENT DOCUMENTS

| 4,671,954 | 6/1987 | Goldberg et al. | 424/450 |
|---|---|---|---|
| 4,752,464 | 6/1988 | Lieberman et al. | 424/1.1 |
| 4,849,209 | 7/1989 | Lieberman et al. | 424/1.1 |
| 4,889,707 | 12/1989 | Day et al. | 424/1.1 |
| 5,011,797 | 4/1991 | Day et al. | 501/33 |
| 5,026,538 | 6/1991 | Lieberman et al. | 424/1.1 |
| 5,061,475 | 10/1991 | Lieberman et al. | 424/1.1 |
| 5,061,641 | 10/1991 | Shochat et al. | 530/362 |
| 5,102,990 | 4/1992 | Rhodes | 530/391.5 |
| 5,128,119 | 7/1992 | Griffiths | 424/1.1 |
| 5,133,956 | 7/1992 | Garlich et al. | 424/1.1 |
| 5,216,130 | 6/1993 | Line et al. | 530/362 |
| 5,225,180 | 6/1993 | Dean et al. | 424/1.1 |

FOREIGN PATENT DOCUMENTS 8907456 8/1989 WIPO.

OTHER PUBLICATIONS

Wang, et al., Reduced Hepatic Accumulation of Radiolabeled Monoclonal Antibodies with Indium-111-Thioether-Poly-L-Lysine-DTPA-Monoclonal Antibody-TP41.2F(ab')2, The Journal of Nuclear Medicine, vol. 33, No. 4, pp. 570–574, Apr. 1992.

Evers, et al., Somatostatin and Analogues in the Treatment of Cancer, Ann. Surg., vol. 213, No. 3, pp. 190–198, Mar. 1991.

Longnecker, Somatostatin and Octreotide: Literature Review and Description of Therapeutic Activity in Pancreatic Neoplasia, Drug Intelligence and Clinical Pharmacy, vol. 22, pp. 99–106, Feb. 1988.

Bauer, et al., SMS 201–995: A Very Potent and Selective Octapeptide Analogue of Somatostatin with Prolonged Action, Life Sciences, vol. 31, pp. 1133–1140, Jun. 30, 1982.

Grassetti, et al., The Determination of Thiols and of Total Glutathione in Human Blood Using 6,6'Dithiodinicotinic Acid (CPDS), Biochemical Medicine 12, pp. 149–153, 1975.

Rodney Jue et al., Addition of Sulfhydryl Groups to *Escherichia coli* Ribosomes by Protein Modification with 2-Iminothiolane (Methyl 4-Mercaptobutyrimidate), American Chemical Society, vol. 17, No. 25, 1978.

R. N. Perham et al., Reaction of Tobacco Mosaic Virus with a Thiol-containing Imidoester and a possible application to X-ray Diffraction Analysis, J. Mol. Biol. (1971) 62, pp. 415–418.

(List continued on next page.)

Primary Examiner—Robert L. Stoll
Assistant Examiner—Lara E. Chapman
Attorney, Agent, or Firm—Senniger, Powers, Leavitt & Roedel

[57] ABSTRACT

A radiolabeled protein composition adapted for radiation therapy which comprises a radioisotope and a protein material containing about 6 or more percent amino acids which have a sulfhydryl-containing side chain. A method for carrying out radiation synovectomy of arthritic joints. Rhenium radiolabeled protein microspheres are administered which contain cysteine and other amino acids. A method for radiolabeling a protein composition whereby the composition is treated with a reducing agent capable of reducing disulfides to sulfhydryls prior to radiolabeling.

22 Claims, 8 Drawing Sheets

OTHER PUBLICATIONS

Wei Jia, A Study of Rhenium Labeled HSA Microspheres as a Radiation Synovectomy Agent, M. S. Thesis, University of Missouri, Nov. 1991.

Ehrhardt et al., Microspheres of Human Serum Albumin Labelled by a Specific Linker Technology for use in Radiation Synovectomy, *Journal of Nuclear Medicine*, vol. 32, No. 5, May 1991.

Ratcliffe et al., "Albumin Microspheres for Intra-articular Drug Delivery", *J. Pharm. Pharmacol.*, 39(4), 290–5 (C.A. 106(22): 182574) (1987).

Sledge et al., Intra-articular Radiation Synovectomy, Clinical Orthopaedics and Related Research, 37–40, No. 182, Jan.–Feb. 1984.

Sledge et al., Experimental Radiation Synovectomy by 165Dy Ferric Hydroxide Marcoaggregate, Arthritis and Rheumatism, vol. 20, No. 7, (Sep.–Oct. 1977).

Johnson et al., Absorbed Dose Profiles for Radionuclides of Frequent Use in Radiation Synovectomy, Arthritis and Rheumatism, vol. 34, No. 12, pp. 1521–1529 (Dec. 1991).

Radiopharmaceuticals, Soc'y Nuc. Med., pp. 282–295, New York (1980).

White, Properties & Manufacturing Techniques of Human Serum Albumin–Microspheres, M. S. Cer. Eng. Thesis, University of Missouri-Rolla, pp. 6–9, 42–49 (May 1991).

Minghetti et al., Molecular Structure of Human Albumin Gene is Revealed by Nucleotide-Sequence within q11–22 of Chromosome 4, J. Biol. Chem., vol. 261, No. 15, pp. 6747–6753 (1986).

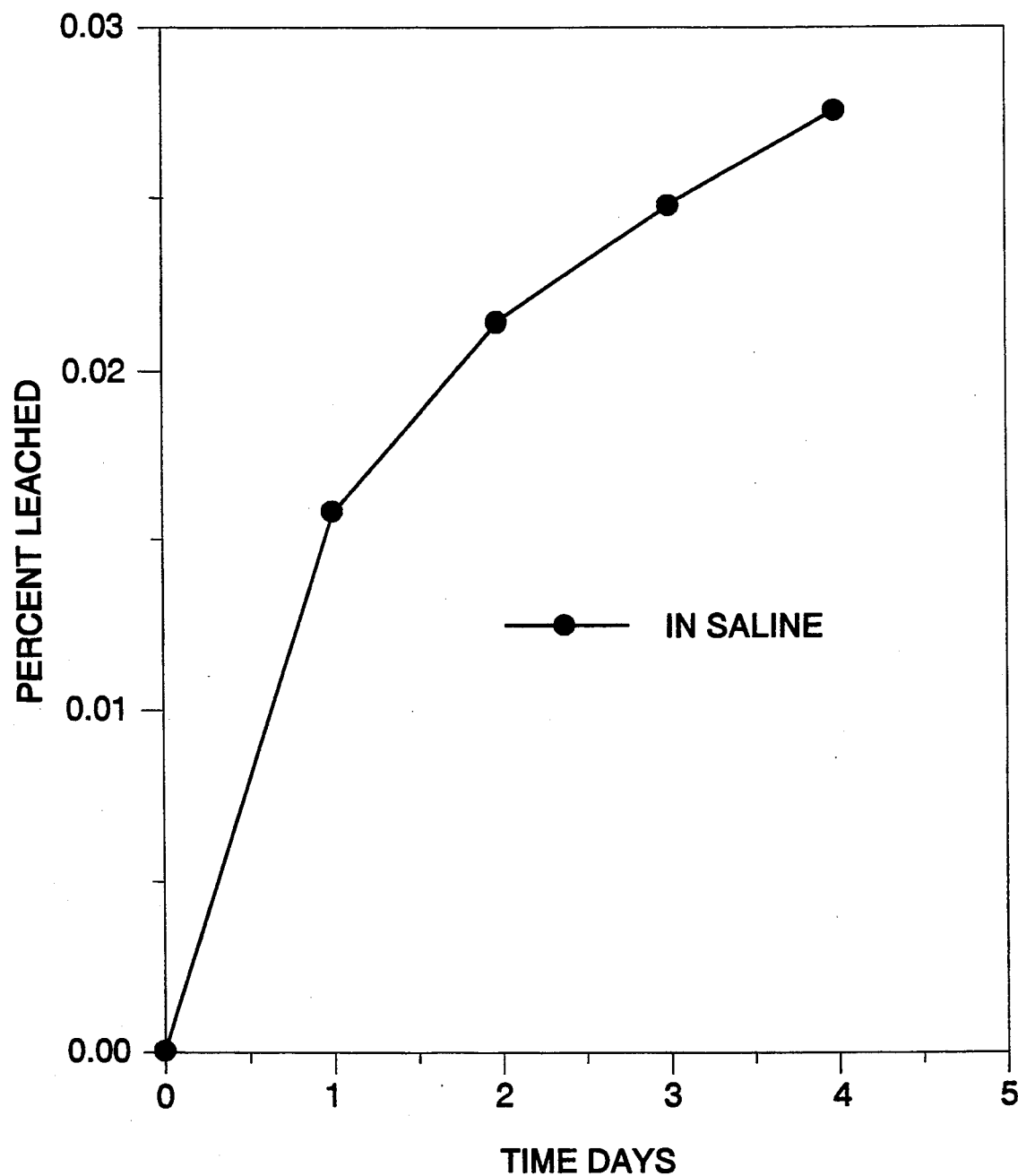

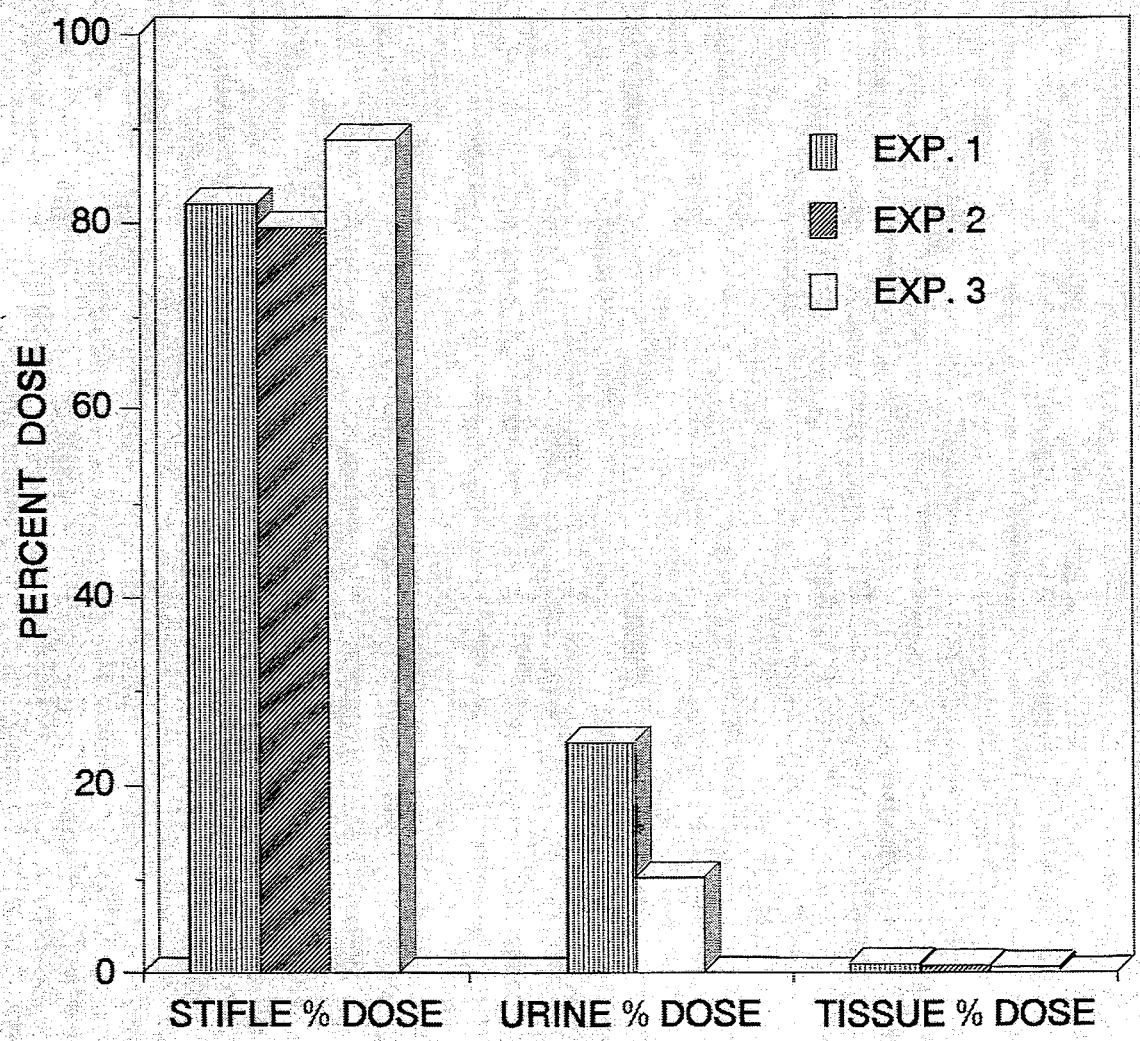

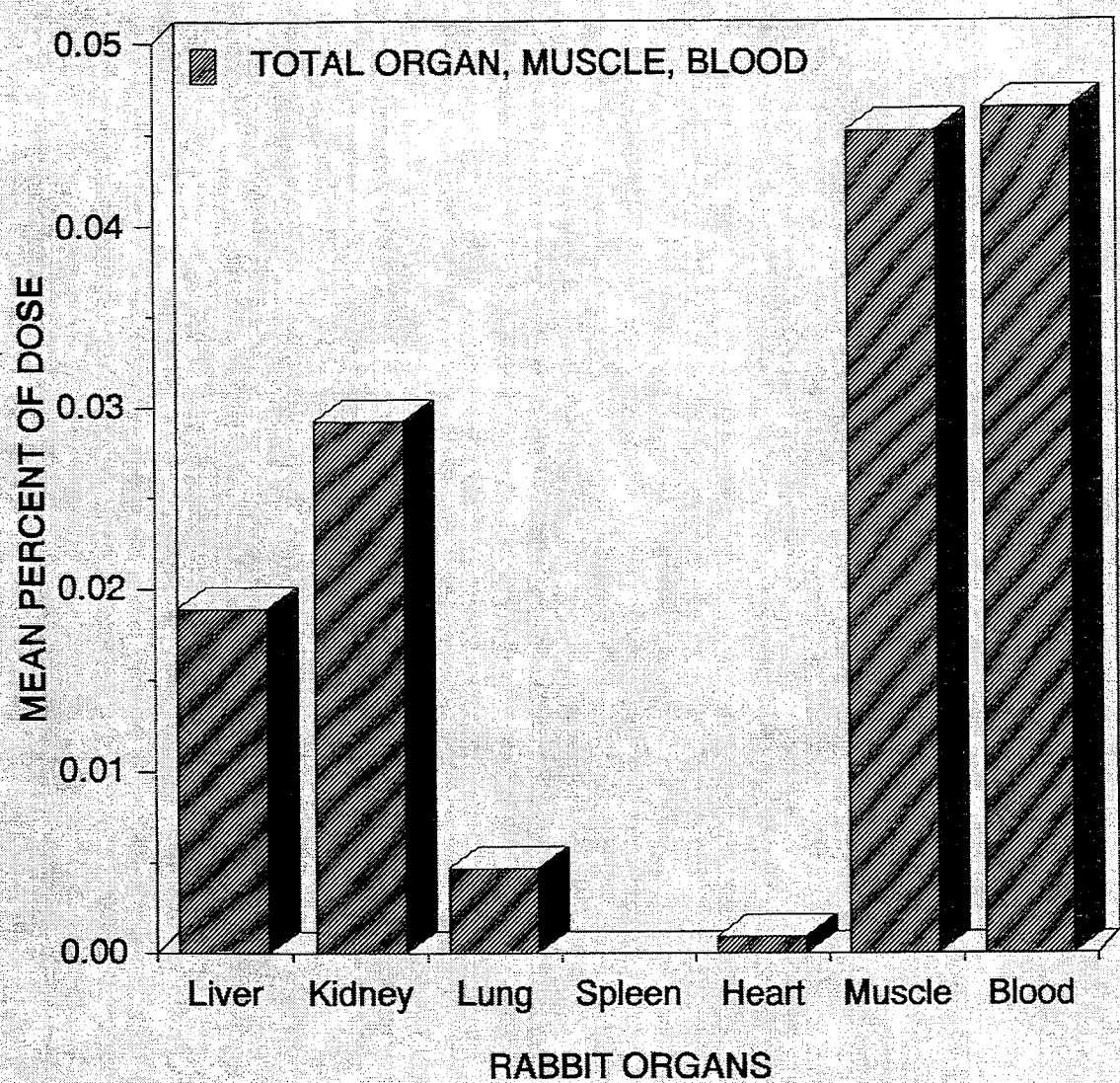

RADIOLABELED PROTEIN COMPOSITION AND METHOD FOR RADIATION SYNOVECTOMY

BACKGROUND OF THE INVENTION

This invention relates to radiolabeled protein compositions being adaptable for radiation therapy, diagnosis and research. The invention also relates to a method of using protein microspheres for radiation synovectomy.

It is estimated that 1-3% of the population in the United States has rheumatoid arthritis (hereinafter RA), which can cause chronic synovial inflammation and can lead to progressive loss of joint function and significant disability. RA has heretofore been treated primarily by surgical or chemical synovectomy. Surgical synovectomy consists of the surgical removal of the inflamed lining of the joint (synovium), and in general can be expected to provide limited periods of symptomatic relief. It is technically difficult, however, to completely remove the synovium from the joint. Surgical synovectomy entails risks such as infection, hemorrhage and anesthetic problems. Surgery often requires prolonged periods of hospitalization and rehabilitation for recovery. Surgery is expensive, invasive and is not attractive for repeat treatments. Proposed methods of chemical synovectomy use osmic acid, cobra venom or other agents and often have significant systemic effects such as injury to the articular cartilage.

Radiation synovectomy has been proposed, for example, by Johnson et al., *Absorbed Dose Profiles for Radionuclides of Frequent use in Radiation Synovectomy*, Arthritis and Rheumatism, Vol. 34, No. 12, p. 1521 (Dec. 1991), for the treatment of RA and offers a viable alternative to surgery and chemical synovectomy. Radioisotopes are commonly used for research, treatment and diagnosis in the field of nuclear medicine. Such applications include liver, lung, bone and tumor scanning and radiotherapy. Radiation synovectomy radiotherapy involves delivering a lethal dose of beta radiation to diseased synovial membrane.

Radiation synovectomy has been used in Europe but certain disadvantages have made it generally unacceptable for use in the United States. Radiation synovectomy treatments in Europe have employed yttrium-90 radiocolloids which emit beta radiation but do not emit gamma radiation. It has therefore not been possible to track radiation leakage and the spread of radioactivity within the patient using an external gamma ray detector. Additionally, prior methods of radiation synovectomy often suffer from high radioactivity leakage rates of the particulate preparations which serve as carriers for the radioactivity. Radiation synovectomy treatments have therefore lacked the ideal source of radiation and the ideal radioactivity carrier.

Microspheres formed from human serum albumin have been proposed for use as radioactivity carriers in connection with the use of radioactivity for diagnostic purposes, e.g., lung scanning, as in *Radiopharmaceuticals*, Soc'y Nuc. Med., p. 282, New York (1980). Specifically, human serum albumin microspheres have been radiolabeled with Tc-99m and injected or otherwise allowed to enter a mammalian host. A gamma ray detector has then been used to image certain areas of the patient. Microspheres labeled with Tc-99m, however, are not suitable for radiation therapy, and radiation synovectomy treatment for RA in particular; Tc-99m emits gamma radiation, not the beta radiation which is lethal to diseased synovial membrane.

Accordingly, a need has existed for an improved method and materials, including radioisotope carrier, for use in radiation synovectomy treatment of RA. A need has also existed for an improved radioisotope carrier for use in research, treatment and diagnosis in the field of nuclear medicine.

SUMMARY OF THE INVENTION

Among the several objects of the invention, therefore, are the provision of an improved method for treating RA which is relatively free of harmful side effects and the provision of an improved radioactivity carrier which is adaptable for use in a wide variety of diagnostic, treatment and research applications in the field of nuclear medicine. Other objects and features of the invention will be in part apparent and in part pointed out hereinafter.

Briefly, therefore, the invention is directed to a radiolabeled protein composition adapted for radiation therapy or diagnosis of a mammal which comprises a beta radiation emitting radioisotope and a protein material containing at least 6 molar percent amino acids residues having a sulfhydryl-containing side chain.

The invention is further directed to a substantially spherical radiolabeled protein microsphere adapted for radiation therapy of a mammal comprising a radioisotope selected from the group consisting of Re-186, Re-188 and the combination of Re-186 and Re-188, and protein material containing at least about 25 molar percent cysteine and at least about 25 molar percent amino acids having a nitrogen-containing side chain.

The invention is further directed to a substantially spherical radiolabeled microsphere adapted for radiation therapy of a mammal consisting essentially of a radioisotope selected from the group consisting of Re-186, Re-188 and the combination of Re-186 and Re-188, and protein material containing at least about 35 molar percent lysine and at least about 35 molar percent cysteine.

The invention is further directed to a method for carrying out radiation synovectomy of arthritic joints, comprising administering to a mammal affected with an arthritic joint substantially spherical microspheres comprising a protein material containing cysteine, said microspheres being radiolabeled with a beta radiation emitting radioisotope selected from the group consisting of Re-186, Re-188 and the combination of Re-186 and Re-188.

The invention is further directed to an improvement in a method for radiolabeling a protein composition containing amino acids having a sulfhydryl-containing side chain for use in radiotherapy and diagnosis in mammals. The improvement comprises contacting the composition with a reducing agent capable of reducing disulfides to sulfhydryls and thereafter radiolabeling the composition.

BRIEF DESCRIPTION OF THE DRAWINGS

FIG. 6 is a plot of the results of leaching tests reflecting the chemical durability of microspheres of the invention.

FIG. 7 is a plot of the radioactivity distribution in the urine of rabbits tested using the microspheres and method of the invention.

FIG. 8 is a plot of the radioactivity distribution in rabbits tested using the microspheres and method of the invention.

DETAILED DESCRIPTION OF THE INVENTION

Figure 1:
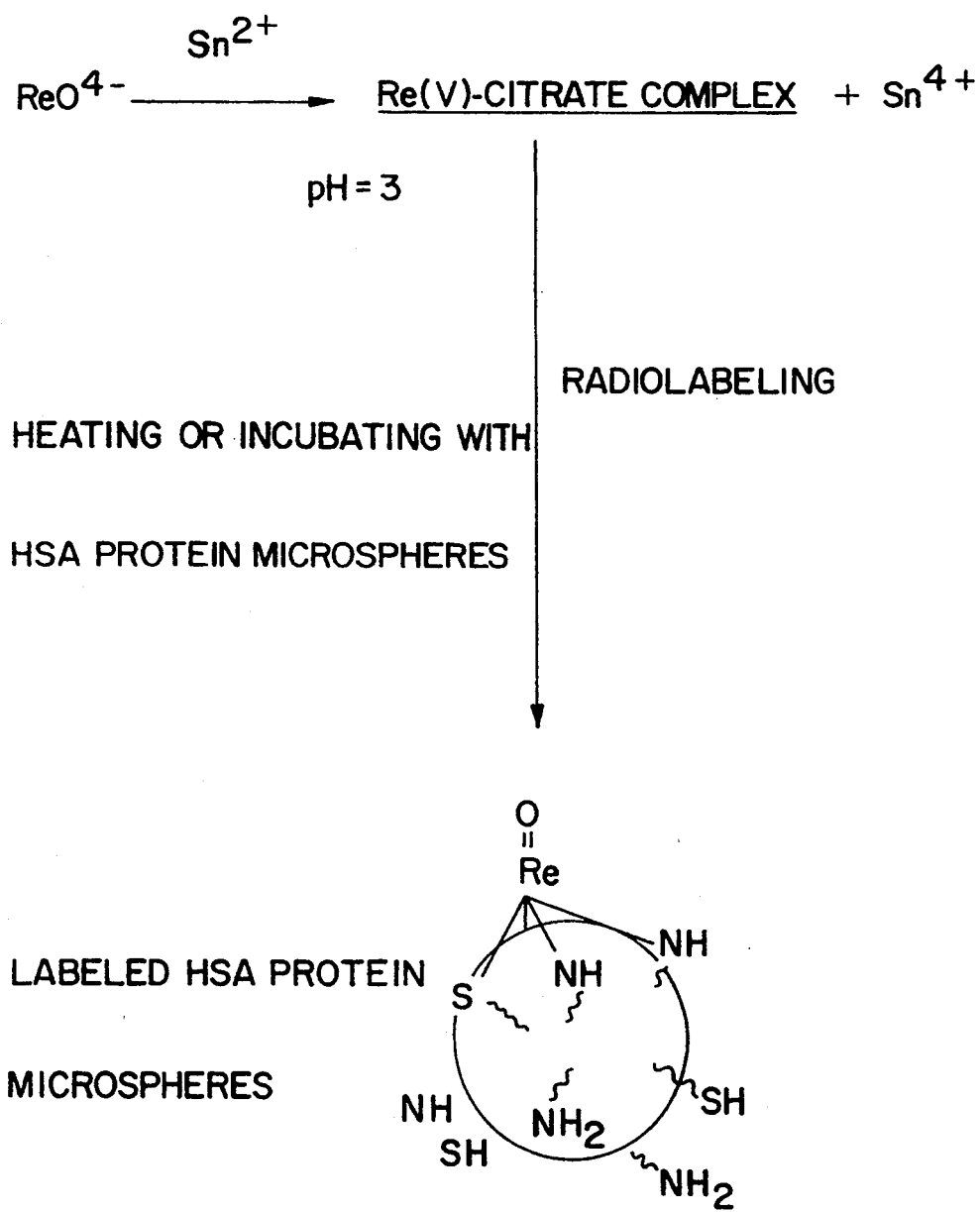
FIG. 1 is a schematic of a method for radiolabeling protein microspheres.

"Protein compositions" as used herein designates both those compositions which comprise albumin and other proteins separated from blood products or other fluids from a mammal and those compositions which comprise chemically synthesized or microbially manufactured proteins. "Synthetic" as used herein in reference to proteins and microspheres means produced from materials other than human blood products. All percentages expressed herein are molar percent unless otherwise indicated.

It has been discovered that protein compositions radiolabeled with Re-186 or Re-188 are effective for radiotherapy. In particular it has been discovered that protein microspheres radiolabeled with Re-188 or Re-186 are effective for use in the treatment of rheumatoid arthritis (RA) by radiation synovectomy. It has also been discovered that microspheres comprising proteins having a predetermined minimum concentration of amino acid residues having sulfhydryl-containing side chains have advantages over previously known protein microspheres and other radioactivity carriers used in treatment, diagnosis and research in the field of nuclear medicine.

The composition and method of the invention involve the use of rhenium as a source of radiation attached to protein compositions. Re-186 and Re-188 emit gamma rays, and therefore provide the advantage of being detectable in the host's system by detection methods known in the field of nuclear medicine including the sodium iodide method, germanium method or other known methods of gamma ray detection. Re-186 and Re-188 decay by $\beta$-emission which provides the lethal dose necessary for radiotherapy. Re-186 decays into a stable daughter product and is characterized by a half-life of about 90 hours, a strong $\beta$-emission (1.07 MeV), and an essentially monoenergetic 137 keV imageable gamma ray emission (9%). Re-188 decays into a stable daughter product and is characterized by a half-life of about 17 hours, a strong $\beta$-emission (2.13 MeV), a 155 keV imageable gamma-ray emission (15%).

Re-188 is preferred over Re-186 for certain applications such as radiation synovectomy because concerns relating to containment of radioactivity over time are not as great due to Re-188's shorter half-life, i.e., the time period during which Re-188 leakage is potentially dangerous to the host is shorter. Additionally, Re-188's higher beta energy provides the necessary penetration to treat large joints such as the human knee. Re-188 is also advantageously readily producible from a W-188/Re-188 radioisotope generator analogous to known Mo-99/Tc-99m generators and consequently can be readily generated on-site and provided as a "no carrier added" radioisotope. Both Re-186 and Re-188 are adaptable to radiolabeling by attachment thereof to protein compositions, as described hereinbelow.

The radiolabeled protein compositions of the invention may take various geometric forms including nonuniform globules, generally rectangular conformations, irregular conformations, or substantially spherical microspheres. Substantially spherical microspheres are preferred for radiation synovectomy for reasons including their being more readily sizable, classifiable, and more resistant to fragmentation, than other conformations. As to sizability, there are ongoing studies and indications that microspheres of certain narrow size ranges of diameters such as, for example, 10 to 30 microns, may be most appropriate for synovectomy of a particular joint. It is advantageous, therefore, to be able to select microspheres from a predetermined range of diameters, if it is believed that a certain range of diameters, or combination of ranges, is most appropriate for the particular application.

Three methods for producing protein microspheres radiolabeled with Re or other radioisotopes are 1) the formation of microspheres from radiolabeled material, 2) incorporation of various radionuclides during the formation of microspheres and, preferably, 3) attachment of radionuclides to preformed protein microspheres. The preparation of protein microspheres for subsequent radiolabeling in accordance with the preferred method involves emulsification or formation of a suspension of aqueous protein droplets in oil, gelation or solidification, by application of heat, of the aqueous protein droplets into rigid microspheres and separation and sizing of solidified microspheres. The preparation of HSA microspheres in this manner is known in the art and described in *Radiopharmaceuticals*, Soc'y Nuc. Med., pp. 282-83, New York (1980) and in White, *Properties & Manufacturing Techniques of Human Serum Albumin Microsphere*, M. S. Cer. Eng. Thesis, U. of Mo.-Rolla, p.1-38 (991). This latter reference, at pages 39-61, also describes an alternative method, the drop tube system, suitable for producing protein microspheres of the invention. The method of making the protein microspheres is not in itself critical to the invention. Described below are examples illustrating specific methods for preparing protein microspheres.

The protein microspheres of the invention have a diameter of less than about 100 microns, preferably between about 3 and about 50 microns, more preferably between about 5 and about 30 microns, and most preferably between about 10 and about 20 microns. As discussed above, different sizes and size distributions of microspheres are desired for different applications. Research is ongoing with respect to the relationship between microsphere size and efficacy for radiation therapy, as measured by, for example, containment within the joint being treated. The density of the microspheres is generally close to the density of water, preferably between about 1.0 and about 1.05 g/cc. The density is such that the microspheres are readily suspendable in the carrier solution used for injection into the affected joint of the host.

In accordance with one embodiment of the invention, novel protein compositions have been devised for use as radioactivity carriers in therapeutic, diagnostic and research applications of nuclear medicine. One particular application for these compositions is the treatment of RA referred to hereinabove and as described in detail hereinbelow. These novel compositions, however, are adaptable for other radiotherapeutic and diagnostic applications in mammals where radioactivity carriers may be used including, for example, liver, lung and kidney cancer treatment and lung scanning.

The compositions of the invention comprise proteins which have a predetermined minimum proportion, about 6%, of amino acid residues having sulfhydryl-containing side chains. The preferred amino acid having a sulfhydryl-containing side chain is cysteine [$HSCH_2CH(NH_2)$]. A major advantage of these compositions is that their composition facilitates attachment of radioisotopes. Without being bound to any one theory, it is suspected that Re-186 and Re-188 radionuclides, in particular, bind to protein compositions primarily at sulfhydryl-containing side chains, as are present in cysteine. The sulfhydryl-containing side chain of cysteine is not involved in the internal peptide bond, and, being located at one end of the amino acid, is available for the formation of external bonds. A high concentration of available sulfhydryl-containing side chains on the composition surface, therefore, is thought to favor labeling efficiency and stability of the bond between the radioisotope and the composition.

HSA which, as indicated above, has been previously proposed for use in radioactivity carriers for certain applications, has about 35 cysteine amino acid residues out of a total of about 585 amino acid, residues according to Minghetti et al., *Molecular Structure of Human Albumin Gene Is Revealed by Nucleotide Sequence within q11-22 of Chromosome 4*, J. Biol. Chem., Vol. 261, No. 15, p. 6753 (1986). Compositions formed substantially entirely from HSA, therefore, contain less than about 6% cysteine. It has been discovered that compositions having an increased content of amino acid residues having a sulfhydryl-containing side chain, such as cysteine relative to HSA have certain advantages as described herein. The compositions of the invention contain at least 6% amino acid residues having a sulfhydryl-containing side chain, preferably at least about 10% amino acid residues having a sulfhydryl-containing side chain, more preferably at least about 25% amino acid residues having a sulfhydryl-containing side chain, and most preferably at least about 35% amino acid residues having a sulfhydryl-containing side chain.

It is also believed that the presence of amino acid residues characterized by nitrogen-containing side chains may favor labeling efficiency and stability of the bond between the radioisotope and the composition. The beneficial effect of nitrogen-containing side chains is believed to involve interaction among the nitrogen-containing side chains, sulfhydryl-containing side chains and radionuclides, or at least to otherwise promote the desired binding between the composition and the radionuclides. Compositions of the invention therefore preferably, but not necessarily, contain a proportion of amino acid residues having nitrogen-containing side chains in addition to the amino acid residues having sulfhydryl-containing side chains as described above. It is also preferred that the compositions of the invention contain at least about 10% amino acid residues having nitrogen-containing side chains, preferably at least about 25% amino acid residues having nitrogen-containing side chains, and more preferably at least about 35% amino acid residues having nitrogen-containing side chains. For these compositions, it is preferred that the ratio of amino acid residues having a sulfhydryl-containing side chain to amino acid residues having nitrogen-containing side chains be in the range of about 1:1 to about 1:3.

It is believed that the particular amino acid or amino acids selected for the amino acid residues having a nitrogen-containing side chain is not critical, but the preferred amino acid is lysine [$NH_2(CH_2)_4CH(NH_2)COOH$]. One preferred composition contains a combined cysteine and amino acid having a nitrogen-containing side chain content which approaches 100%. The most preferable of such compositions contains about 50% cysteine and about 50% lysine. Other amino acids having nitrogen-containing side chains are substitutable in whole or in part for lysine in the compositions. These amino acids include, non-exclusively, arginine, asparagine, glutamine, histidine and tryptophan.

Though protein compositions of the invention are preferably formed primarily from cysteine or cysteine in combination with an amino acid having a nitrogen-containing side chain such as lysine, the compositions may also contain certain proportions of other amino acids or combinations thereof, depending on the particular application, availability of material, and other factors. The function of amino acids other than those having sulfhydryl- or nitrogen-containing side chains, as currently understood, is primarily to provide mass to the compositions. In addition to lysine and cysteine, appropriate amino acids for use in connection with these compositions may be selected from the group which includes, non-exclusively, alanine, arginine, asparagine, aspartic acid, glutamine, glutamic acid, glycine, histidine, isoleucine, leucine, methionine, phenylalanine, proline, serine, threonine, tryptophan, tyrosine and valine. As stated above, certain of these amino acids have nitrogen-containing side chains and therefore may be included in the preferred compositions of the invention. Certain amino acids are appropriate for use in the compositions of the invention, irrespective of whether they have sulfhydryl-containing or nitrogen-containing side chains, so long as they are metabolizable, non-toxic, non-antigenic, and otherwise compatible with compositions for use as in vivo radioactivity carriers.

The compositions comprise combinations of amino acids which are independent amino acid chains cross-linked, for example cysteine or polycysteine cross-linked to lysine or polylysine, upon formation of the composition. The compositions may also comprise polyamino acid chains having different amino acids in the same chain, as with a polyamino acid chain of ten amino acids, five lysines and five cysteines. Polyamino acids used in connection with the invention may be of a predetermined sequence.

The molecular weight of polyamino acid chains used in forming the compositions of the invention is in the range of about 1000 to about 50,000 grams per mole, preferably in the range of about 10,000 to about 20,000 grams per mole. Polyamino acid chains for these compositions have in the range of about 10 to about 400 amino acids per chain, preferably in the range of about 50 to about 200 amino acids per chain, and most preferably about 100 amino acids per chain. Chains which are too long or have too high of a molecular weight are difficult to dissolve during the formation of the compositions. The protein material used to form the compositions may be prepared any of various known or hereinafter developed methods including chemical synthesis and microbial manufacture.

Increased radionuclide-to-carrier bond strength and stability provided by the above-described compositions render the compositions less susceptible than other radioactivity carriers to enzymatic attack in the body and therefore less susceptible to in vivo leaching of radioactivity into the host's system. For example, the strong Re-to-sulfhydryl and/or Re-to-amine bond thought to be characteristic of Re-radiolabeled cysteine/lysine compositions may reduce the tendency of Re to be oxidized in vivo to perrhenate. Compositions formed primarily from lysine, cysteine and/or other suitable amino acids are preferred over HSA due to the foregoing advantages and due to immunogenetic and infection-related concerns with using blood products such as human albumin.

The amino acid or combination of amino acids selected for the compositions are preferably metabolizable, non-toxic, and non-antigenic. The L isomer of the selected amino acid is preferred over the D isomer because the L conformations are naturally occurring. Naturally occurring isomers may be more compatible with the host, readily metabolizable, and, being indigenous to mammals, more readily approved for use in mammals by governmental authorities. It is also preferred that the amino acid or combination of amino acids, when formed and solidified into a composition, be sufficiently chemically durable in vivo such that significantly harmful amounts of radioactivity are not leached from radiolabeled compositions formed therefrom into the host's system during a period of about five half-lives of the attached radioisotope.

The preparation of the preferred protein compositions, when formed into microspheres, can be achieved by the emulsification method, the drop-tube method, or other suitable methods as is the case with HSA microspheres. Although the method by which the microspheres are made is not critical to the invention, the emulsification method as described herein.

It has been discovered that extensive washing and pretreatment of the compositions, both HSA compositions and other protein compositions, significantly improve the chemical durability and overall labelability of the compositions. Washing the compositions thoroughly with saline and a detergent is thought to remove loosely bound protein molecules. It is most preferred that the detergent be a non-ionic detergent, specifically, sodium dodecyl sulfate, but other detergents are suitable. Chemical durability in vivo is improved in that loosely bound proteins are removed and therefore not available to be released, i.e., leached, within the host's system.

Treatment of the compositions with a reducing agent has been found to significantly improve the efficacy of the compositions for attachment of radionuclides and subsequent use for nuclear medical applications. Pretreatment of the compositions in this manner reduces in vivo leakage of the radionuclides. Without being bound to any one theory, it is suspected that this treatment serves to reduce disulfide bonds, formed from sulfhydryl groups upon heating of the compositions during preparation, back to sulfhydryl groups. This reduction is believed to substantially increase the number of available bonding sites for attachment of radioisotopes to the compositions. In particular, it is believed that this pretreatment facilitates the reformation of sulfhydryl groups having affinity for the radiolabel to be attached (Re(V)). Reducing agents capable of this type of reduction are well known in the art, including, for example, $\beta$-mercaptoethanol (98% 2-hydroxyethyl-mercaptan available from Sigma Chemical Co.) and DTT (99% DL-dithiothreitol available from Sigma Chemical Co.). The reducing agent is provided in a concentration in the range of from about 0.2 to about 10%, preferably in the range of from about 0.5 to about 5%, and most preferably in the range of from about 0.5 to about 2%. The compositions are suspended in the reducing agent solution and heated in a boiling water bath for about 30 to about 90 minutes.

Figure 2:
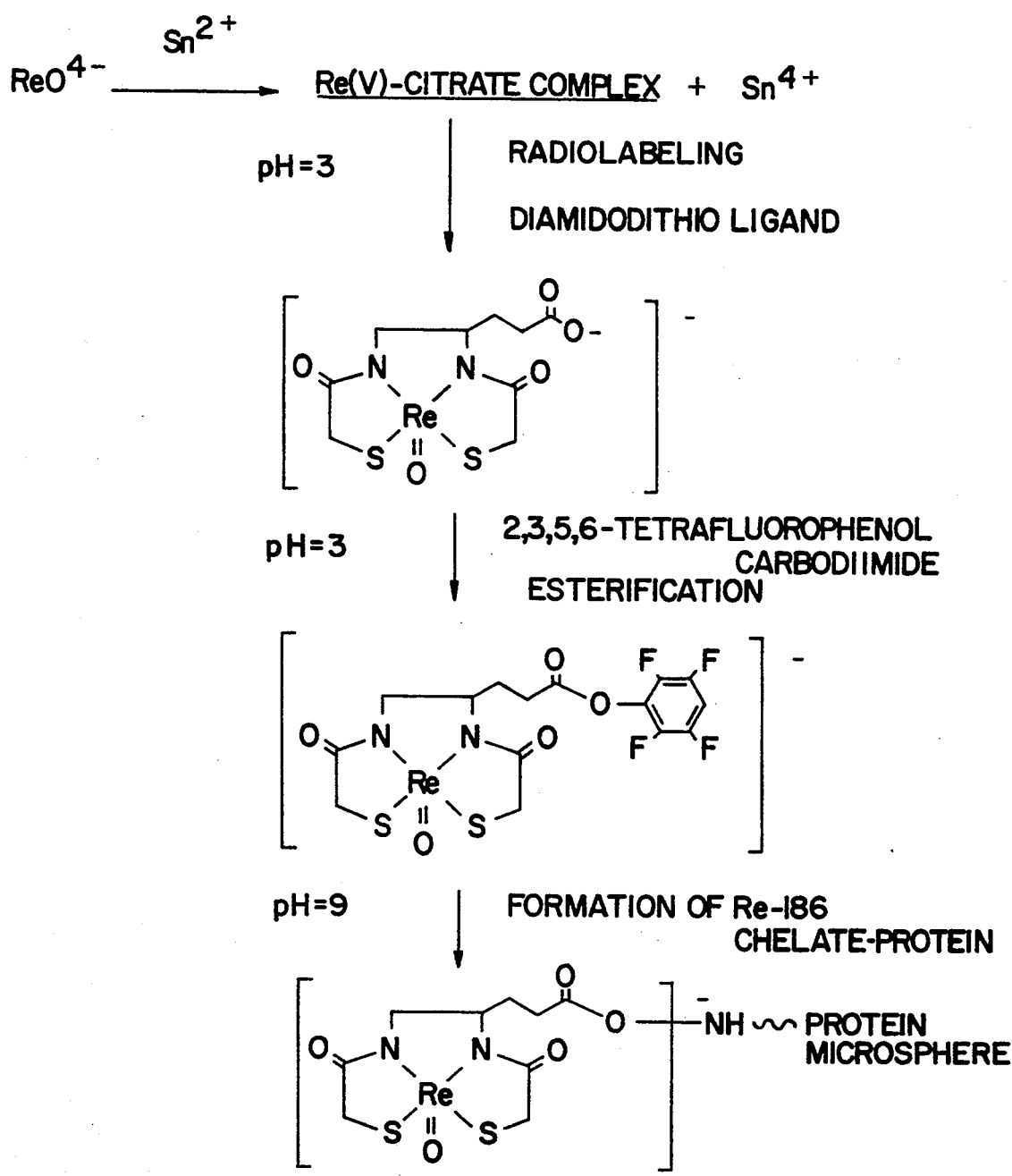
FIG. 2 is a schematic of a second method for radiolabeling protein microspheres.

Protein compositions for use in connection with the method of the invention can be radiolabeled directly. By direct labeling, Re-186 or Re-188 is reduced from the VII oxidation state to the V oxidation state and bound directly to connecting groups on the compositions. Without being bound to any one theory, radioactive oxo Re(V), reduced from perrhenate, is believed to form a stable complex (transfer ligand) which is readily attachable to thiol and amine groups on protein molecules. This preferred labeling method and the presumed mechanism are further described in FIG. 1. Each milligram of the protein compositions can be labeled with up to about 1 to about 4 millicuries Re, but generally is labeled with about 50 to about 500 microcuries Re, preferably with about 100 to about 400 microcuries Re, and most preferably with about 100 to about 300 microcuries Re. Specifically, a transfer ligand is obtained by combining a Re reducing agent such as tin (II) chloride 99%, a Re stabilizing agent such as citric acid and an antioxidant such as gentisic acid in a reaction vial. The vial is purged with nitrogen gas and deoxygenized, deionized water is added to form a solution having a pH of about 3. The desired amount of radioactive perrhenate (comprising Re-186 or Re-188), generally about 50 to about 500 microcuries per milligram of composition to be labeled, is transferred into the reaction vial and reduced upon heating for about 30 minutes in a boiling water bath. The Re(V) citrate complex solution is then transferred into a glass tube containing agitated protein composition suspension. The glass tube is placed into a boiling water bath; stirring and heating are maintained for about 1 hour. The Re-labeled compositions are then separated from the aqueous supernatant Radiolabeling may also be accomplished in accordance with the method and mechanism wherein a stable Re complex is formed and then attached to the composition as set forth in FIG. 2.

Radiolabeled protein compositions produced as described above may be used in connection with the method of the invention for radiation synovectomy treatment of RA. In accordance with the method of the invention, radiolabeled microspheres prepared as described are administered to afflicted joints of a mammal by intra-articular injection or other suitable means of administration. The dosage for treatment of an afflicted joint depends on various factors including the size of the joint, the progression of the disease, and the tolerance of the patient. The typical dosage is in the range of from about 0.5 to about 20 milligrams of microspheres radiolabeled with about 50 to about 500 microcuries Re per milligram. Upon administration, the microspheres become distributed reasonably uniformly along the synovial membrane and emit beta radiation of sufficient strength to fully irradiate the thickness of the membrane without imparting significant dosage to more distant joint structures. Inasmuch as the thickness of the diseased membrane varies in different joints, the present invention makes possible the injection of different size microspheres for a knee than for a finger joint, for example.

The following examples illustrate certain preferred embodiments of this method and the efficacy of the compositions of the invention for radiation therapy, including treatment, diagnosis and research, in mammals. The protocol and experimental methods followed were approved by the University of Missouri-Columbia Animal Care and Use Committee and complied with the federal Animal Welfare Act.

EXAMPLE 1

HSA microspheres acceptable for use in connection with the method of the invention were produced by placing 200–300 ml of cottonseed oil (USP) in a glass beaker and stirring at about 500 rpm with a 2½ inch propeller-type stirrer. An aqueous solution of 25% HSA at ambient temperature was added to the beaker using a hypodermic syringe with a 25-gauge needle. HSA was added at a volume ratio of 4 ml per liter of oil. The oil/HSA mixture was heated to 135° C. and maintained at that temperature for about 40 minutes while stirring was continued. The oil suspension was cooled to room temperature, diluted with heptane, and the microspheres were isolated by filtration. After several washes with heptane to completely remove the oil, the microspheres were dried.

About 15–20 mg of protein microspheres were placed with a magnetic stir bar into a 10 ml glass tube for pretreatment. Five ml of 1–1.5% $\beta$-mercaptoethanol (98% 2-hydroxyethyl-mercaptan available from Sigma Chemical Co.) and 1 ml of 1% Tween-80 (liquid polyoxoethylene sorbitan monooleate available from Sigma Chemical Co.) were added to the tube. 0.5–1.0% DTT (99% $DL$-dithiothreitol available from Sigma Chemical Co.) may be substituted for the $\beta$-mercaptoethanol. The microsphere suspension was heated in a boiling water bath and stirred for 45–60 minutes. The supernatant was removed by centrifugation and the microspheres were washed with deionized water and allowed to dry.

Transfer ligand was obtained by placing about 6 mg tin (II) chloride 99%, about 55 mg citric acid, about 50 mg sodium citrate, and about 20 mg gentisic acid in a 5 ml reaction vial. The vial was purged with nitrogen gas and 1.5 ml of previously deoxygenized, deionized water was added to form a solution of about pH 3. About 1 to 1.5 ml radioactive perrhenate containing about 5 millicuries of high specific activity Re-186 (about 1 to 3 curies per milligram) or generator-produced Re-188 was transferred into the reaction vial containing transfer ligand and reduced upon heating for about 30 minutes in a boiling water bath. The Re(V) citrate complex solution was promptly transferred into a glass tube containing a micro-stirrer and 1 ml protein microsphere suspension in 0.5% Tween-80 containing 15 mg microspheres. The glass tube was placed into a boiling water bath; stirring and heating were maintained for about 1 hour. The Re-labeled microspheres were separated from the aqueous supernatant through centrifugation and thoroughly washed with deionized water or isotonic saline.

EXAMPLE 2

Polycysteine-polylysine microspheres were produced by placing 200 ml of mineral oil (USP) in a 500 ml glass beaker, stirring with a magnetic stir bar and heating the oil to about 65° C. A 3 ml solution of polypeptide in dichloroacetic acid was added from a 3 ml disposable hypodermic syringe using a 25-gauge needle. The polypeptide was a 50:50 molar mixture of cysteine and lysine. The oil/polypeptide mixture was heated to about 120° C. and maintained at that temperature for about 60 minutes while stirring was continued. The oil suspension was cooled to room temperature and the microspheres were isolated by centrifugation. After several washes with heptane and acetone to completely remove the oil, the microspheres were dried with nitrogen gas.

About 15–20 mg of protein microspheres were placed with a magnetic stir bar into a 10 ml glass tube for pretreatment. Five ml of 1–1.5% $\beta$-mercaptoethanol (98% 2-hydroxyethylmercaptan available from Sigma Chemical Co.) and 1 ml of 1% Tween-80 (liquid polyoxoethylene sorbitan monooleate available from Sigma Chemical Co.) were added to the tube. 0.5–1.0% DTT (99% $DL$-dithiothreitol available from Sigma Chemical Co.) may be substituted for the $\beta$-mercaptoethanol. The microsphere suspension was heated in a boiling water bath and stirred for 45–60 minutes. The supernatant was removed by centrifugation and the microspheres were washed with deionized water and allowed to dry.

Transfer ligand was obtained by placing about 6 mg tin (II) chloride 99%, about 55 mg citric acid, about 50 mg sodium citrate, and about 20 mg gentisic acid in a 5 ml reaction vial. The vial was purged with nitrogen gas and 1.5 ml of previously deoxygenized, deionized water was added to form a solution of about pH 3. About 1 to 1.5 ml radioactive perrhenate containing about 5 millicuries of high specific activity Re-186 (about 1 to 3 curies per milligram) or generator-produced Re-188 was transferred into the reaction vial containing transfer ligand and reduced upon heating for about 30 minutes in a boiling water bath. The Re(V) citrate complex solution was promptly transferred into a glass tube containing a micro-stirrer and 1 ml protein microsphere suspension in 0.5% Tween-80 containing 15 mg microspheres. The glass tube was placed into a boiling water bath; stirring and heating were maintained for about 1 hour. The Re-labeled microspheres were separated from the aqueous supernatant through centrifugation and thoroughly washed with deionized water or isotonic saline.

EXAMPLES 3–6

Figure 3:
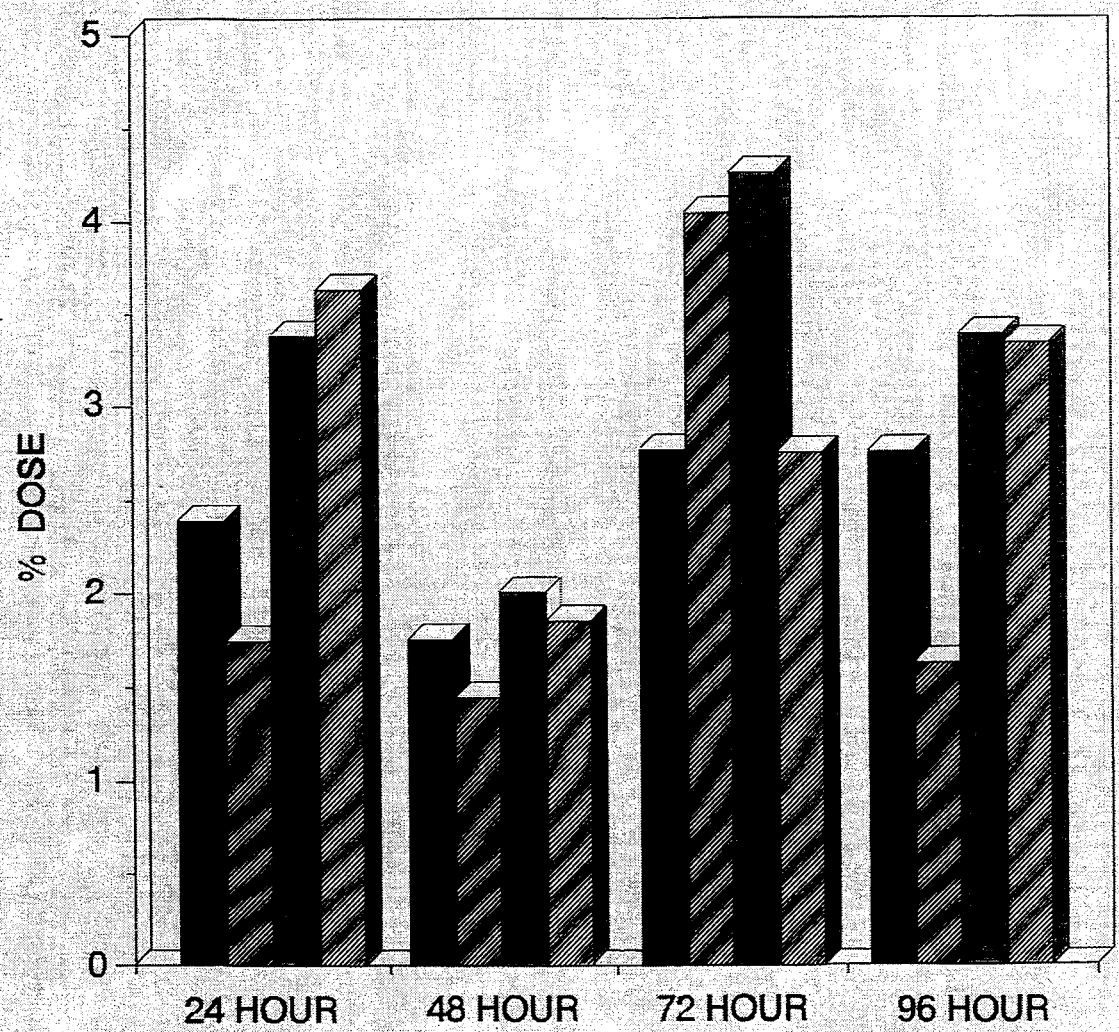
FIG. 3 is a plot of the radioactivity distribution in the urine of rabbits tested using the microspheres and method of the invention.
Figure 4:
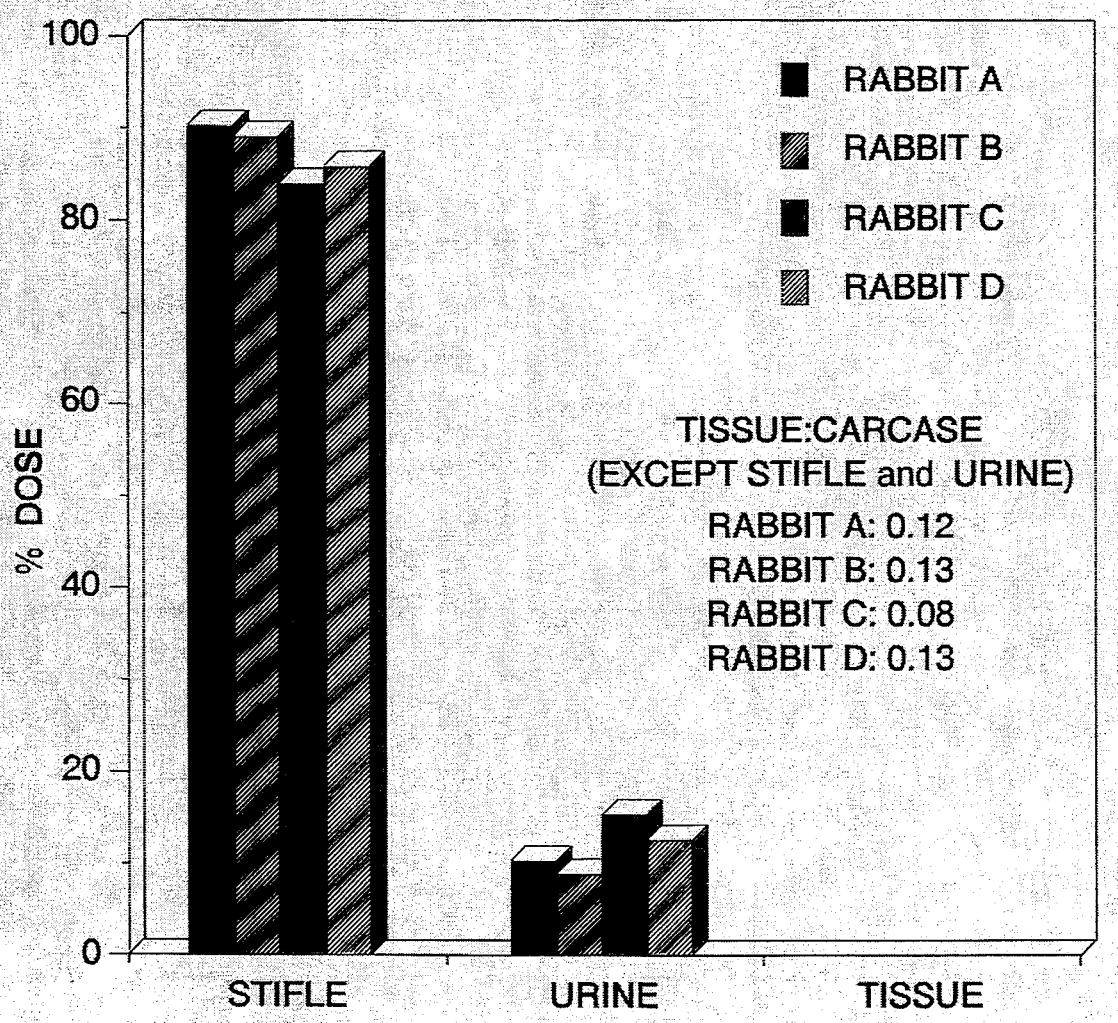
FIG. 4 is a plot of the radioactivity distribution in rabbits tested using the microspheres and method of the invention.
Figure 5:
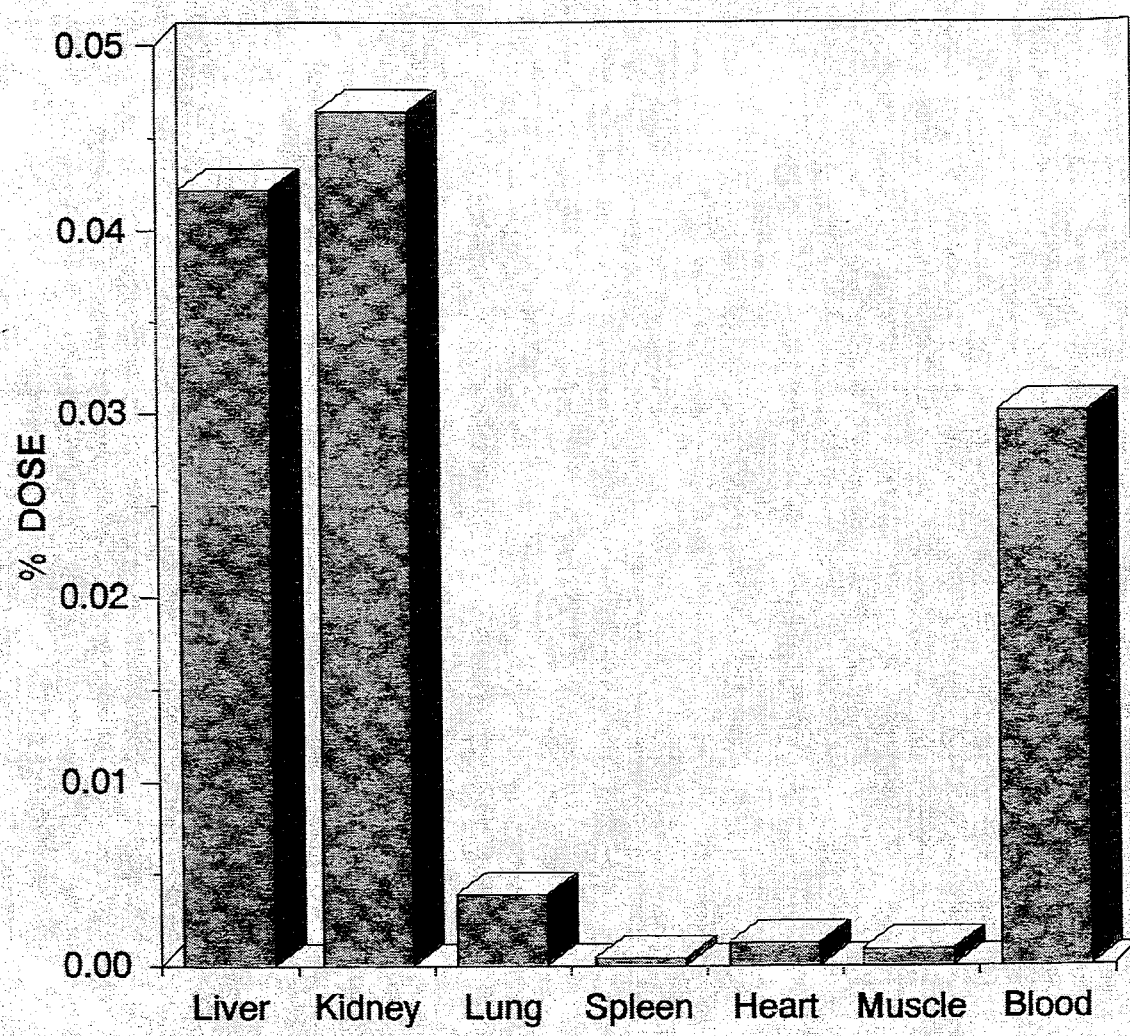
FIG. 5 is a plot of the radioactivity distribution in rabbits tested using the microspheres and method of the invention.

Microspheres containing about 50% polylysine and about 50% polycysteine by mole percent were prepared and directly labeled with Re-186 as described above in Example 2. Each microsphere had a diameter between about 6 and about 80 microns, with about 50% of the microspheres having a diameter between about 10 and about 40 microns. 1–2 mg microspheres suspended in saline solution carrying about 200–400 microcuries were injected, using 1 ml tuberculin syringes, into the rear knee joint (stifle) of each of four New Zealand white rabbits. The radioactivity in the urine of each rabbit as measured daily for four days is presented in FIG. 3. Each rabbit was sacrificed after four days and the data presented in FIGS. 4–5 collected. These data reveal that the percent injected dose remaining in the stifle after 96 hours was as high as 87%, the percent injected dose in the urine averaged about 11%, and the percent injected dose remaining in the tissue was as low as about 0.08%.

EXAMPLE 7

5 mg 50% polylysine and 50% polycysteine microspheres prepared as in Example 2 were placed in saline solution at 37° C. The percent radioactivity leached after each of four days was determined and is reported in FIG. 6. Less than 0.03% of the Re label leached in 96 hours.

EXAMPLE 8

Re-186 labeled HSA microspheres prepared according to the method of Example 1, except that they were not pretreated with β-mercaptoethanol or DTT, and having a range of diameter from 1 to 50 microns, were suspended in isotonic saline solution and injected into the rear stifles of each of four New Zealand white rabbits using 200 microliter glass syringes. Each rabbit was sacrificed after 24 hours and the data presented in FIG. 7 collected. In a second in vivo study using microspheres which had not undergone pretreatment, leakage to the urine was significantly higher, about 30%, after 4 days.

EXAMPLE 9

Re-186 labeled HSA microspheres were prepared and injected as set forth in Example 8, except that the microspheres were suspended in Angiovist instead of isotonic saline solution. Each rabbit was sacrificed after 24 hours and the data presented in FIG. 7 collected.

EXAMPLE 10

Re-186 labeled HSA microspheres were prepared and injected as set forth in Example 9, except that only microspheres having diameters of approximately 23 microns were used. Each rabbit was sacrificed after 24 hours and the data presented in FIG. 7 collected. The mean percent dose of radioactivity distributed at 24 hours in certain rabbit organs for Examples 8–10 was determined and is presented in FIG. 8.

In view of the above, it will be seen that the several objects of the invention are achieved.

Although specific examples of the present invention and its application are set forth herein, it is not intended that they are exhaustive or limiting of the invention. These illustrations and explanations are intended to acquaint others skilled in the art with the invention, its principles, and its practical application, so that others skilled in the art may adapt and apply the invention in its numerous forms, as may be best suited to the requirements of a particular use.

We claim:

1. A radiolabeled protein composition adapted for radiation therapy or diagnosis of a mammal, comprising a beta radiation emitting radioisotope and a protein composition comprising at least 10 molar percent amino acid residues having a sulfhydryl-containing side chain, said composition being sufficiently chemically durable in vivo such that significantly harmful amounts of radioactivity are not leached from the composition into a host's system during a period of about five half-lives of the attached radioisotope when the composition is injected into the host's system.

2. The composition of claim 1, said composition comprising at least about 25 molar percent amino acid residues having a sulfhydryl-containing side chain.

3. The composition of claim 2, said composition comprising at least about 35 molar percent amino acid residues having a sulfhydryl-containing side chain.

4. The composition of claim 2, said composition further comprising at least about 25 molar percent amino acid residues having a nitrogen-containing side chain.

5. The composition of claim 1 wherein said beta radiation emitting radioisotope is Re-186, Re-188, or a combination of Re-186 and Re-188.

6. The composition of claim 1 wherein said composition is a substantially spherical microsphere.

7. A radiolabeled protein microsphere adapted for radiation therapy of a mammal comprising a substantially spherical microsphere comprising a protein composition and a radioisotope selected from the group consisting of Re-186, Re-188, and the combination of Re-186 and Re-188, said microsphere having a diameter between 10 microns and 30 microns.

8. The microsphere of claim 7 wherein the microsphere comprises at least about 25 molar percent cysteine and at least about 25 molar percent amino acid residues having a nitrogen-containing side chain.

9. The microsphere of claim 8 wherein said cysteine and said amino acid residues having a nitrogen-containing side chain combine to form about 100% of the microsphere.

10. A substantially spherical radiolabeled protein microsphere adapted for radiation therapy of a mammal comprising a substantially spherical microsphere comprising at least about 35 molar percent lysine and at least about 35 molar percent cysteine and a radioisotope selected from the group consisting of Re-186, Re-188, and the combination of Re-186 and Re-188.

11. A radiolabeled protein composition adapted for radiation therapy or diagnosis of a mammal comprising a beta radiation emitting radioisotope and a protein composition comprising at least 6 molar percent cysteine, said composition being sufficiently chemically durable in vivo such that significantly harmful amounts of radioactivity are not leached from the composition into a host's system during a period of about five half-lives of the attached radioisotope when the composition is injected into the host's system.

12. The composition of claim 11 comprising at least about 10 molar percent cysteine and at least about 10 molar percent amino acid residues having a nitrogen-containing side chain.

13. The composition of claim 11 wherein said beta radiation emitting radioisotope is Re-186, Re-188, or a combination of Re-186 and Re-188.

14. The composition of claim 11 wherein said composition is a substantially spherical microsphere.

15. The microsphere of claim 7 which is sufficiently chemically durable in vivo such that significantly harmful amounts of radioactivity are not leached from the composition into a host's system during a period of about five half-lives of the attached radioisotope when the composition is injected into the host's system.

16. A radiolabeled protein composition adapted for radiation therapy of a mammal comprising a beta radiation emitting radioisotope and a protein composition comprising at least 10 molar percent amino acid residues having a sulfhydryl-containing side chain, said composition being a solidified protein composition which is suspended in a carrier solution for injection and administration by distribution of the solidified composition to an area of a host to receive radiation therapy.

17. The composition of claim 11, said composition comprising at least about 25 molar percent amino acid residues having a sulfhydryl-containing side chain.

18. The composition of claim 17 wherein said beta radiation emitting radioisotope is Re-186, Re-188, or a combination of Re-186 and Re-188.

19. The composition of claim 16 wherein said composition is a substantially spherical microsphere.

20. The composition of claim 16 having a density between about 1.0 and about 1.05 g/cc.

21. The composition of claim 4 wherein the ratio of amino acid residues having a sulfhydryl-containing side chain to amino acid residues having a nitrogen-containing side chain is in the range of 1:1 to 3:1.

22. A radiolabeled protein microsphere adapted for radiation therapy of a mammal comprising a spherical protein microsphere consisting of 50 molar percent polylysine and 50 molar percent polycysteine, said polylysine and said polycysteine being polyamino acid chains consisting of between about 10 and about 400 amino acid residues per chain, and a radioisotope attached to said microsphere selected from the group consisting of Re-186, Re-188, and the combination of Re-186 and Re-188, said microsphere having a diameter between about 6 microns and about 80 microns.

* * * * *